(12) United States Patent
Heppler (10) Patent No.: US 7,341,596 B2
(45) Date of Patent: Mar. 11, 2008

(54) WIRE GUIDES FOR A SCALPEL

(76) Inventor: J. Scott Heppler, 610 N. 58th Ave., Yakima, WA (US) 98908

(*) Notice: Subject to any disclaimer, the term of this patent is extended or adjusted under 35 U.S.C. 154(b) by 694 days.

(21) Appl. No.: 10/386,638

(22) Filed: Mar. 11, 2003

(65) Prior Publication Data

US 2004/0181246 A1  Sep. 16, 2004

(51) Int. Cl.
*A61B 17/32* (2006.01)
(52) U.S. Cl. ............... 606/167; 606/172; 7/161
(58) Field of Classification Search ........... 606/167, 606/170, 185; 30/240, 123.3, 127, 340; 604/164.01; 7/161
See application file for complete search history.

(56) References Cited

U.S. PATENT DOCUMENTS

| 1,567,908 | A | * | 12/1925 | Brigham | ............ 294/50.6 |
| 3,596,300 | A | * | 8/1971 | D'Amico | ............ 7/106 |
| 4,922,610 | A | * | 5/1990 | Szabo | ............ 30/125 |
| 5,450,670 | A | * | 9/1995 | Sakai | ............ 30/298.4 |
| 5,628,117 | A | * | 5/1997 | Glesser | ............ 30/298.4 |
| 5,843,108 | A | * | 12/1998 | Samuels | ............ 606/167 |
| 6,974,467 | B1 | * | 12/2005 | Gonzales, Jr. | ............ 606/167 |

* cited by examiner

*Primary Examiner*—Anhtuan T. Nguyen
*Assistant Examiner*—Elizabeth Houston
(74) *Attorney, Agent, or Firm*—Stratton Ballew PLLC

(57) ABSTRACT

A scalpel guide system for any bladed surgical instrument. A pair of wire guides attach to a scalpel, for controlled travel of the scalpel along the wire. The wire guides of the scalpel guiding system are especially useful as an enhancement to the "Seldinger technique," a common surgical procedure employed for the percutaneous placement of elongated, tubular devices, with the aid of a guidewire or a wire. The scalpel can be any knife-like surgical device, conventionally including a blade attached to a handle. The scalpel guiding system preferably includes a pair of wire guides, each extending from the blade of the scalpel, or alternatively the handle of the scalpel. The scalpel can be disposable, as can the blade, independent of the scalpel. The wire can be any guidewire or filament, as conventionally employed in surgical techniques that involve the insertion of such a wire or strand. The wire is engageable by the scalpel mounted pair of wire guides. This engagement allows the user or surgeon to move the scalpel along the wire in a controlled and guided manner, for precise cutting or incising, as required for the needed procedure or operation.

11 Claims, 13 Drawing Sheets

WIRE GUIDES FOR A SCALPEL

TECHNICAL FIELD

The invention relates to a scalpel guide system for any bladed surgical instrument, and more particularly to a set of wire guides attached to a scalpel, for controlled travel of the scalpel along the wire.

BACKGROUND OF THE INVENTION

There are many percutaneous medical devices that function to evacuate air or fluid from body cavities. Conversely, other such devices function to administer a substance, such as a drug, into the body cavity or into a vascular lumen. Most of these percutaneous devices are elongated and tubular, sharing a common method of placement over a guide-wire. This common method is known as the "Seldinger technique."

The Seldinger technique has revolutionized the practice of medicine by allowing procedures that were previously done with "open" surgical technique to be performed with "closed," percutaneous technique. As is evident from the following description of the Seldinger technique, the "closed" percutaneous method results in an incision that is just large enough to pass the medical device via a direct tract down to the desired cavity or "lumen."

To perform the Seldinger technique, a hollow hypodermic needle of the necessary length and rigidity to reach the desired body cavity or lumen is passed through the skin surface until the distal tip of the needle is in the cavity or lumen. The needle is often of a much smaller diameter than the medical device that will subsequently be placed in order to minimize damage in the event the cavity or lumen is initially missed. The position of the distal tip of the needle is then verified by aspirating the appropriate body fluid or air into a syringe. In difficult to access cavities or lumens, radiologic guidance can be utilized to confirm placement. A flexible guide-wire is then passed into the proximal hub of the needle, through the lumen of the needle and into the cavity or lumen. Control is maintained at the distal aspect, or exposed length of the guide-wire. Next, the guide-wire is held in position while the needle is withdrawn over the distal aspect of the guide-wire and removed entirely from the distal end of the guidewire.

The elongated, tubular medical device can be too large and too pliable to easily pass over the guidewire, through the needle hole made in the skin and tissues and into the desired body cavity or lumen. Often, a dermatology, commonly referred to as a "skin nick," is then performed with a surgical scalpel blade immediately adjacent to the entry of the guide-wire to enlarge to entry site and allow subsequent passage of the medical device.

A well made skin nick should contain the guidewire and should be large enough to admit the medical device. It should not be so large or so deep as to allow leakage of body fluids around the subsequently placed medical device or to excessively compromise the function of the skin as a barrier to infection. If the nick is made away from the entry site of the wire or is not sufficiently deep, the medical device will not pass over the guidewire and through the skin and tissues easily. If excessive force is used the tip of the medical device can flare and bind at the skin surface.

In spite of the fact that a guidewire leads to the precise place where the skin nick is to be made, the dermatology is often performed with only the visual guidance and the free hand of the operator. In urgent settings, with poorly positioned patients, in poorly lighted rooms, a precisely placed skin nick can require significant concentration at a time when there are other pressing issues with the patient.

Devices have been proposed to minimize these safety and procedural difficulties encountered in performing dermatologies in conjunction with percutaneous placements of guide wires. One such device is found in U.S. Pat. No. 5,843,108, issued to Samuels et al. The Samuels et al. device features a central lumen which passed through both the blade and the handle. This device has several perceived weaknesses. The flexibility of the guidewire requires that the operator hold the wire near the proximal, outside end in order to thread the Samuels et al. scalpel over the guidewire. The potential for the operator to sustain an inadvertent laceration is increased by having the operator place their hand in front of the blade. Another disadvantage of the Samuels et al. device is that is utilizes a custom blade that has a central lumen. Such a blade would be relatively expensive to manufacture.

U.S. Pat. No. 4,955,890 to Yamamoto et al. and U.S. Pat. No. 4,633,860 to Korth et al. also disclose surgical devices that aid in percutaneous procedures. However, like Samuels et al., discussed above, both of these devices require the operator to thread the guidewire through a tubular member, very near surgical blades.

A surgical device is needed that minimized the potential for inadvertent lacerations in the performance of dermatologies. Such a surgical device should be disposable, easily sterilized or easily re-bladed. Ideally, the device should be simple and easy to use, without requiring extensive additional training in technique or procedure. The present invention addresses these needs and will be better understood by reference to the following detailed description taken in conjunction with the accompanying drawings.

DETAILED DESCRIPTION OF SPECIFIC EMBODIMENTS

The present invention provides wire guides for a scalpel, and specifically for a system of guided and controlled movement of the scalpel along a wire. The scalpel guiding system 25 is shown in FIGS. 1 through 22C. The scalpel guiding system is especially useful as an enhancement to the "Seldinger technique." As discussed in the foregoing section, the Seldinger technique is a common surgical procedure employed by a user 26 of a scalpel 27, for the percutaneous placement of elongated, tubular devices, with the aid of a guidewire or a wire 29.

Figure 1:
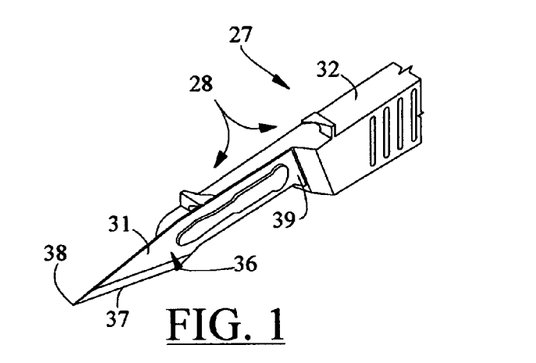
FIG. 1 is a perspective view of a wire guide system for a scalpel, according to an embodiment of the invention.
Figure 2A:
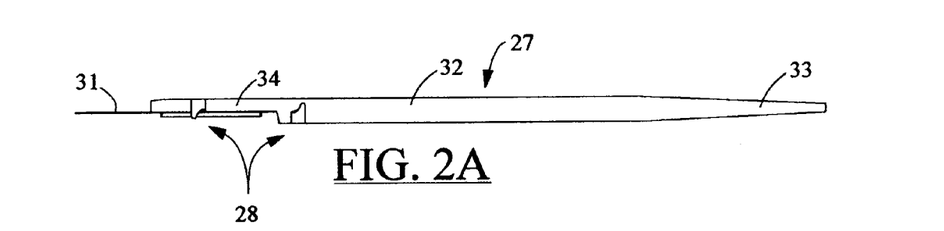
FIG. 2A is a bottom view of a wire guide system for a scalpel, according to an embodiment of the invention.
Figure 2B:
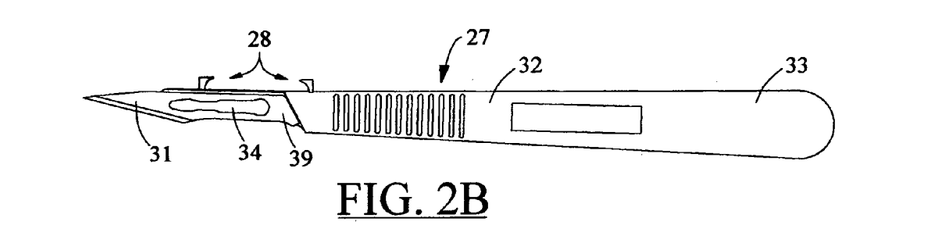
FIG. 2B is a side view of a wire guide system for a scalpel, according to an embodiment of the invention.
Figure 2C:
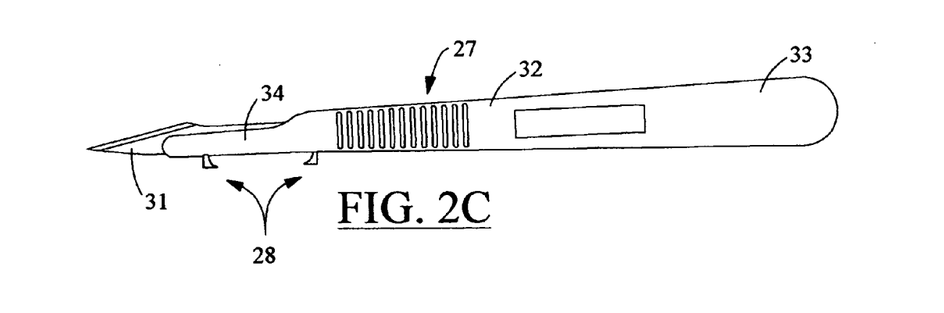
FIG. 2C is a reverse side view of a wire guide system for a scalpel, according to an embodiment of the invention.

As detailed in FIGS. 1 and 2, the scalpel guiding system 25 preferably includes a pair of wire guides 28, each extending from the scalpel 27. For the present invention, the scalpel can be any knife-like surgical device, conventionally including a blade 31 attached to a handle 32. The handle can be formed of a plastic or a metal. Plastic handles are typically employed in disposable scalpel designs, and metal handles utilized in reusable, "autoclaveable" instruments.

The blade 31 can be permanently attached to the handle 32, as typical for disposable handles, or the blade can be replaceable, removable and disposable, as often employed with reusable scalpel handle designs. The blade includes a face 36, which is the side of, or planar, flat portion of the blade, as shown in FIGS. 1, 7, 8, 13 and 17. The blade also includes a cutting edge 37, a point 38 and a shank 39. The shank of the blade is received into or otherwise attached to the handle of the scalpel 27. The attachment of the shank to the handle is typically permanent for most disposable scalpels. For scalpels with removable or replaceable blades, the shank can be disengaged from the handle of the scalpel, to replace the blade.

Figure 3A:
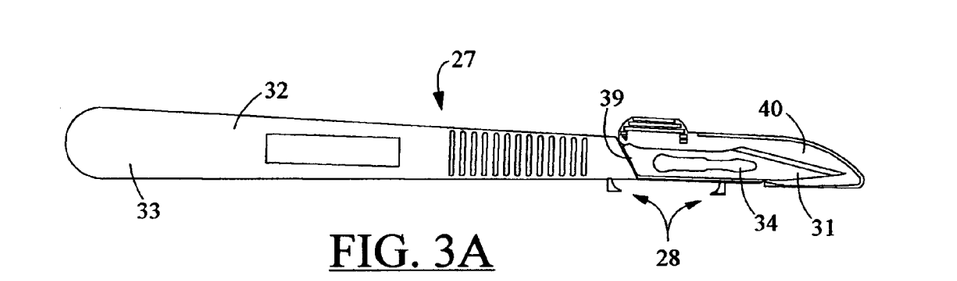
FIG. 3A is a side view of a wire guide system for a scalpel, according to an embodiment of the invention.
Figure 3B:
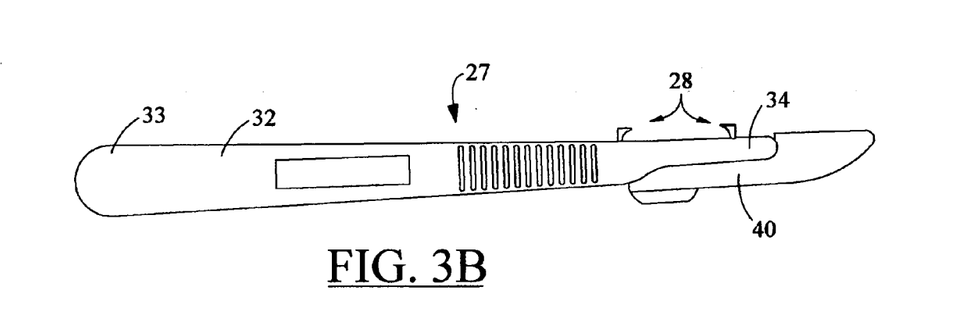
FIG. 3B is a reverse side view of a wire guide system for a scalpel, according to an embodiment of the invention.
Figure 4:
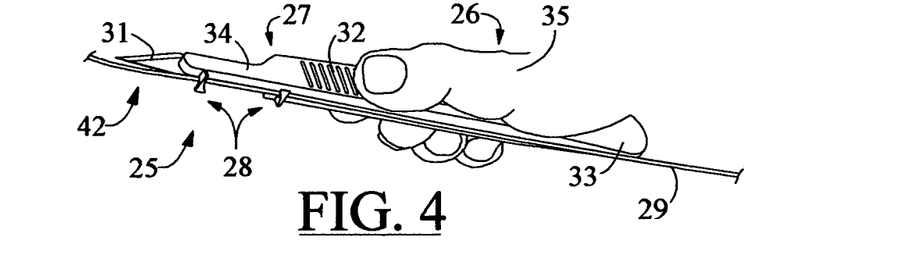
FIG. 4 is a perspective view of a wire guide system for a scalpel, according to an embodiment of the invention.
Figure 12:
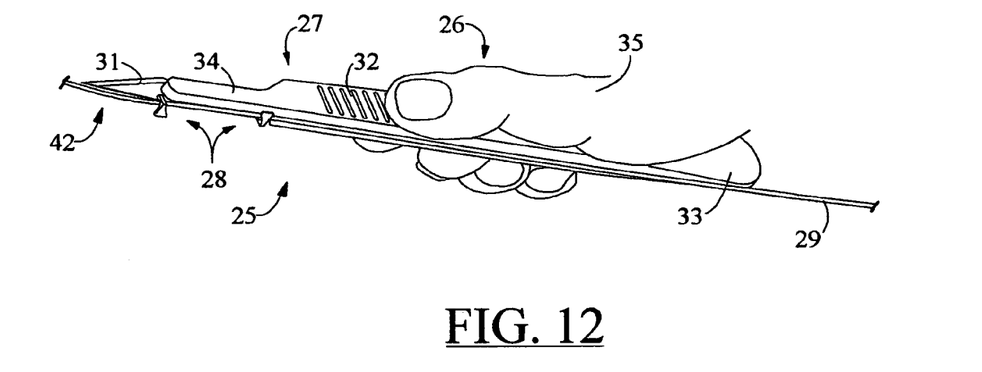
FIG. 12 is a perspective view of a wire guide system for a scalpel, according to an embodiment of the invention.
Figure 16:
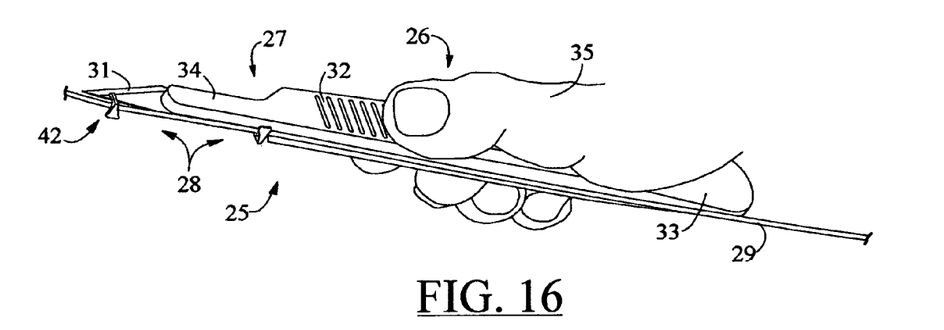
FIG. 16 is a perspective view of a wire guide system for a scalpel, according to an embodiment of the invention.
Figure 17:
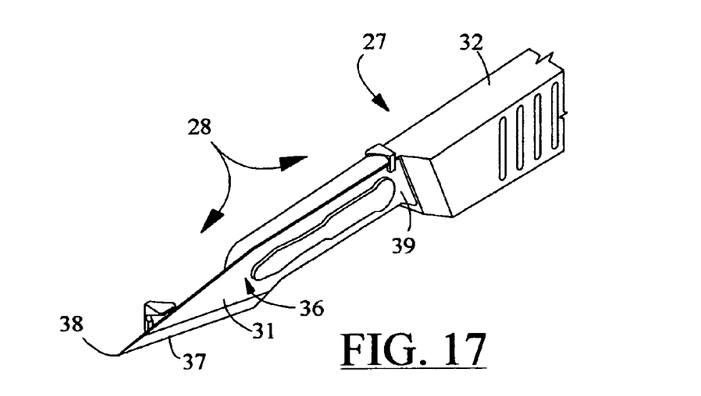
FIG. 17 is a perspective view of a wire guide system for a scalpel, according to an embodiment of the invention.

The handle 32 of the scalpel 27 includes a butt end 33 and a blade end 34, as shown in FIGS. 2B, 2C, 3A, 3B, 10A, 10B, 14A, 14B, 18, 19. The butt end is typically at the termination of the handle 32 and is the end grasped by the hand 35 of the user 26 of the scalpel, as shown in FIGS. 4, 12 and 16. The blade end of the scalpel receives the blade 31 and can also include a shield 40, as shown in FIGS. 3A and 3B. The shield is conventionally detachable, and may be a guard or other conventional device for covering the blade to prevent inadvertent cuts or "sticks" to the user or any other person coming in contact with the scalpel.

As an alternative conventional safety mechanism, the blade 31 may be configured to retract into the handle 32 of the scalpel 27. For this embodiment of the scalpel, the shank 39 is typically slidable within the handle, to cover the cutting edge 37 and point 38 of the blade 31. For an embodiment of the blade, the point can be rounded, as typical for standard #10 blades, or preferably pointed, as found in the standard #11 blade. Though the #11 blade is preferred for use with the present invention, the scalpel guiding system 25 of the present invention is versatile and universal. The scalpel guiding system can be employed with any conventional scalpel or blade configuration.

For a preferred embodiment of the present invention, the pair of wire guides 28 mount to the scalpel 27. The pair of wire guides are adapted to engage a wire 29, as shown in FIGS. 4, 5, 6A, 6B, 9A, 9B, 9C, 12, 16, 18, and 19. The "wire" is broadly defined for the purposes of the present invention, and can be any such guidewire or filament, as conventionally employed in surgical techniques that involve the insertion of such a wire or strand. For example, the wire may be a wound wire, a single metal, plastic or composite strand, a fiber optic cable or bundle, or a braided wire. The wire has a length 42, which is an inherent property for any such wire or filament. In an alternative, any such wire with the ability to meet the basic function of being engageable by the scalpel mounted pair of wire guides, is considered appropriate for use with the present invention.

Figure 6A:
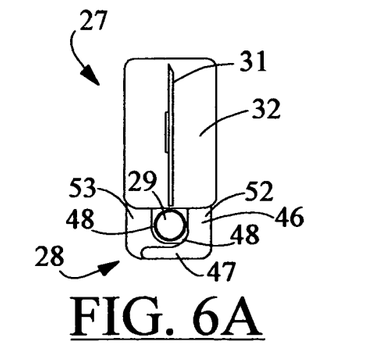
FIG. 6A is an front end view of a wire guide system for a scalpel, according to an embodiment of the invention.

Preferably, each wire guide of the pair of wire guides 28 is generally "L" shaped, as detailed in FIG. 6A. The pair of wire guides engage the wire 29 by virtue of their structure and position on the scalpel 27. Each of the pair of wire guides includes a leg 46, and a foot 47. The leg extends from the scalpel, and the leg is generally parallel to the face 36 of the blade 31. The foot extends from the leg, to complete the L-shape of each of the pair of wire guides. The pair of wire guides may be formed from any material that can engage the wire, preferably without significantly bending or deforming the wire guide in the engagement of the wire.

As additionally shown in FIG. 6A, the wire 29 contacts the pair of wire guides 28 on an inside radius 48. The inside radius forms at the joining of the leg 46 to the foot 47, of the pair of wire guides, which cradles the wire. The curvature of the inside radius is preferably equal to or slightly larger than the wire's radius. The inside radius of the pair of wire guides provides a smooth surface for the wire to slide in a guided and non-binding movement of the wire within the pair of wire guides.

Figure 6B:
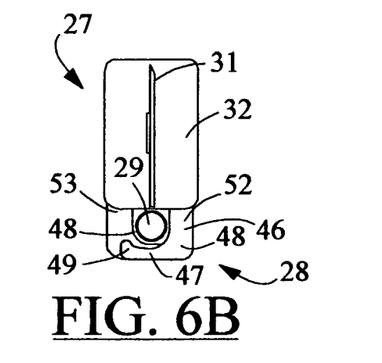
FIG. 6B is an front end view of a wire guide system for a scalpel, according to an embodiment of the invention.
Figure 7:
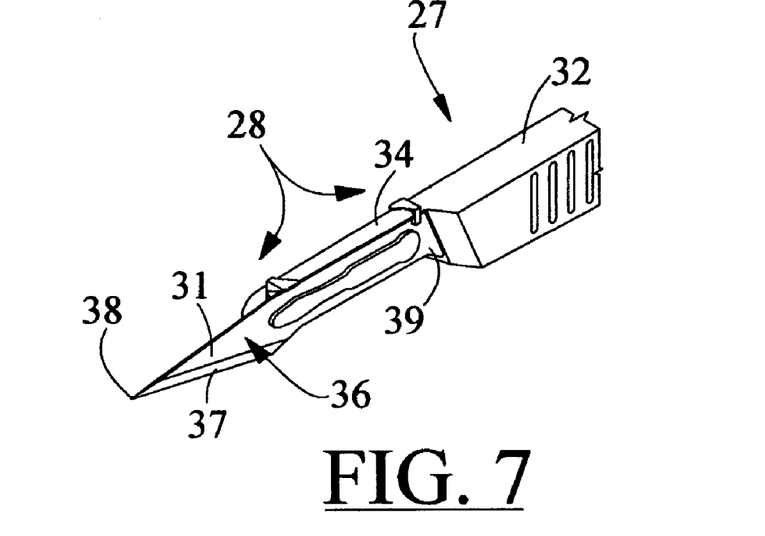
FIG. 7 is a perspective view of a wire guide system for a scalpel, according to an embodiment of the invention.

In an alternative configuration of the pair of wire guides 28, the foot 47 can include a toe 49, as shown in FIG. 6B. The toe and maintains the wire 29 within the pair of wire guides, and forms the pair of wire guides into substantially more of a "J" shape. The toe preferably continues along the inside radius 48 to provide additional containment and grip to the wire.

For a preferred embodiment of the scalpel guiding system 25, as shown in FIGS. 1 through 7, employing a scalpel 27, which is most preferably disposable, the pair of wire guides 28 are formed from the same plastic material as the handle 32 of the scalpel. For the disposable embodiment, the pair of wire guides are most preferably an integral part of the mold of the handle and so does not require any additional forming steps in the manufacture of the handle.

Figure 5:
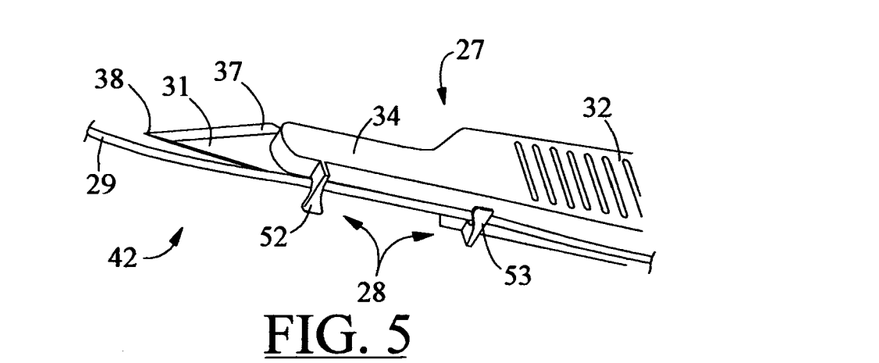
FIG. 5 is a perspective view of a wire guide system for a scalpel, according to an embodiment of the invention.

Preferably, as detailed in FIG. 5, the pair of wire guides 28 includes a forward guide 52 and a rearward guide 53. Most preferably, the rearward or proximal guide extends from the handle 32, proximate the blade end 34, but further along the handle, toward the butt end 33. The forward, or distal guide is also positioned proximate the blade end of the handle, most preferably proximate the cutting edge 37 of the blade 31. The forward guide is close enough to the rearward guide to maintain the wire 29 in tension between the pair of wire guides. Alignment between the wire guides is preferably such that the wire length 42 is suspended in a straight line, engaged between the forward guide and the rearward guide.

Relative to the wire 29, the pair of wire guides 28 substantially oppose each other along the scalpel 27, with the inside radius 48 of the forward guide 52 facing the wire and the inside radius of the rearward guide 53 also facing the wire. This preferred orientation of the inside radius, of both of the pair of wire guides, as shown in FIGS. 6A and 6B, allows the wire to contact the inside radius of both the forward guide and the rearward guide, as the scalpel travels along the wire.

Figure 8:
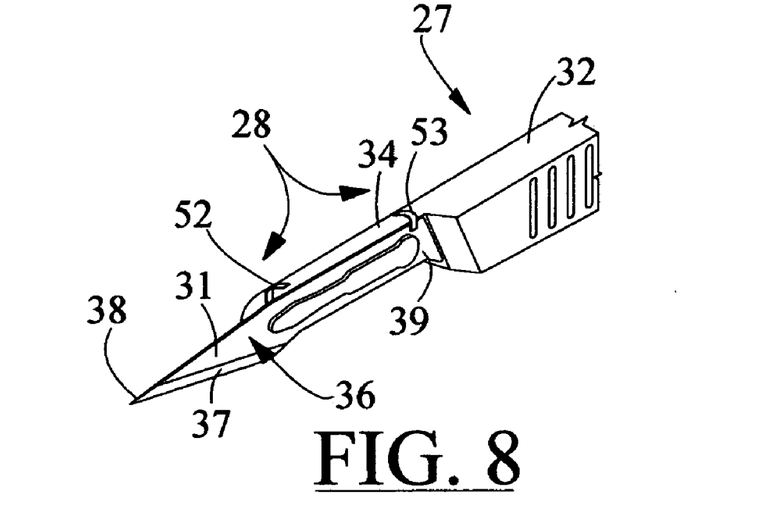
FIG. 8 is a perspective view of a wire guide system for a scalpel, according to an embodiment of the invention.

In an alternative embodiment of the present invention, both of the pair of wire guides 28 can extend from the blade 31 of the scalpel 27, as shown in FIGS. 7, 8, 10A, 10B. This alternative embodiment is useful when a conventional, reusable scalpel is employed, typically with a metal handle, the handle not manufactured with the pair of wire guides as needed for the present invention. The blade of the scalpel can include the pair of wire guides, each embodied by a metal hook 55 extending from the blade. For this embodiment, the pair of wire guides could be stamped from a single piece of metal with the blade and then pressed into the substantially L shape or alternatively the substantially J shape, as desired. Alternatively, as shown in FIG. 8, the pair of wire guides could be soldered, or in some similar way attached, mounted or adherered to the blade. For this alternative, the pair of wire guides are most preferably placed proximate the shank 39 of the blade, with the forward guide 52 proximate to the cutting edge 37 of the blade and the rearward guide 53 proximate to the blade end 34 of the handle, when the blade is attached to the handle, as shown in FIG. 8.

In another alternative embodiment of the present invention, the forward guide 52 of the pair of wire guides 28 extends from the blade 31 of the scalpel 27, while the rearward guide 53 extends from the handle 32 of the scalpel. This alternative embodiment could be employed for both the reusable or the disposable scalpel, and the pair of wire guides could be formed from any material as convenient, the forward guide and rearward guide preferably matching the scalpel and handle material, respectively.

Figure 11A:
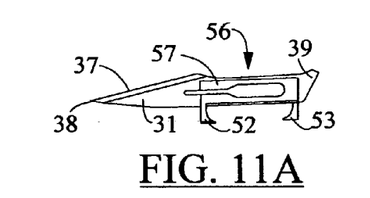
FIG. 11A is a side view of a wire guide system for a scalpel blade, according to an embodiment of the invention.
Figure 11B:
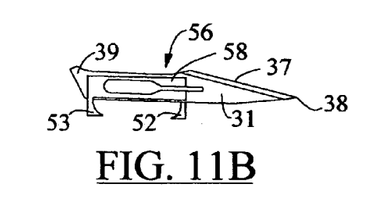
FIG. 11B is a reverse side view of a wire guide system for a scalpel blade, according to an embodiment of the invention.
Figure 11C:
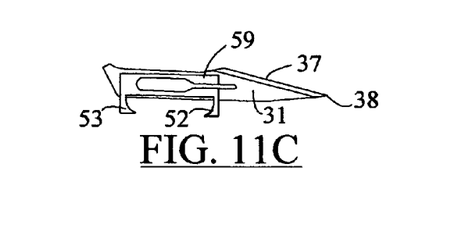
FIG. 11C is a side view of a wire guide system for a scalpel blade, according to an embodiment of the invention.

An additional alternative embodiment of the present invention is shown in FIGS. 11A and 11B. Here, the pair of wire guides 28 extend from a pair of plates 56, which "sandwich" the blade 31 of the scalpel 27. Most preferably, the forward guide 52 extends from a first plate 57, as shown in FIG. 11A, and the rearward guide 53 extends from a second plate 58, as shown in FIG. 11B. Also alternatively, the pair of wire guides could extend from a single plate 59 attached to the blade, as shown in FIG. 11C.

In a most preferred embodiment of the present invention, the pair of wire guides 28 both extend from the handle 32 of the scalpel 27, as discussed above. This embodiment is useful when a conventional blade is employed, typically with a disposable, plastic handle. Conventional metal blades are not manufactured with the pair of wire guides. Preferably, the handle of the scalpel includes the pair of wire guides, with each extending from the handle. The pair of wire guides can be molded with the handle, or otherwise formed from a single piece of plastic or alternatively metal. The blade 31 can be added or affixed to the handle at the time the handle is fabricated, or later, as is typical for conventional, disposable blade scalpel systems.

Figure 13:
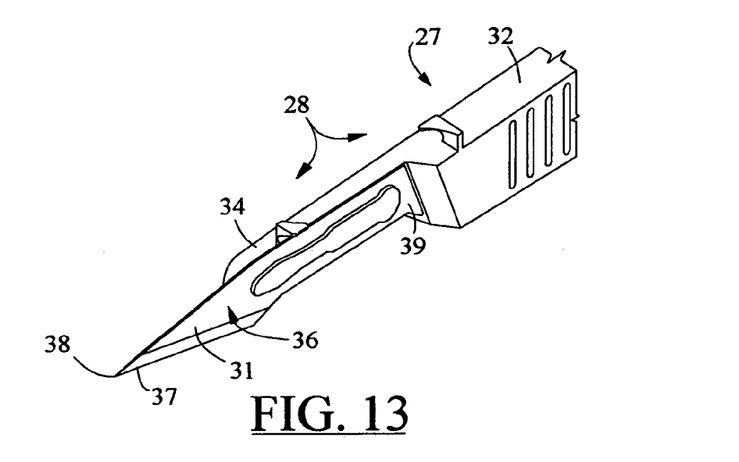
FIG. 13 is a perspective view of a wire guide system for a scalpel, according to an embodiment of the invention.
Figure 14A:
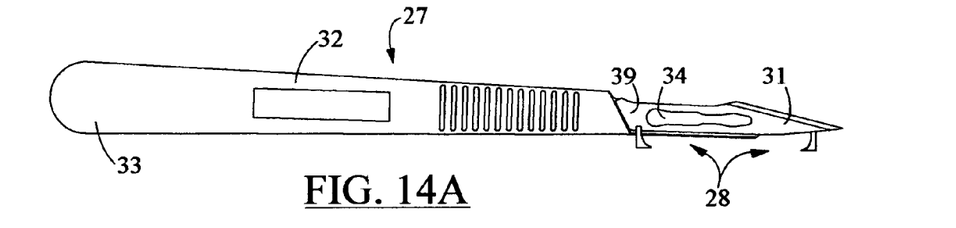
FIG. 14A is a side view of a wire guide system for a scalpel, according to an embodiment of the invention.
Figure 14B:
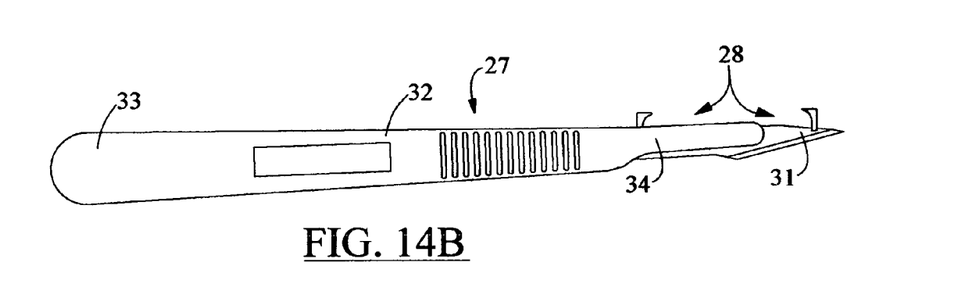
FIG. 14B is a reverse side view of a wire guide system for a scalpel, according to an embodiment of the invention.
Figure 15A:
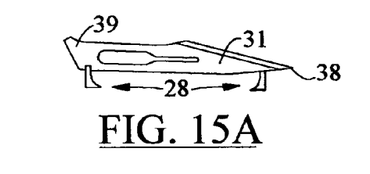
FIG. 15A is a side view of a wire guide system for a scalpel blade, according to an embodiment of the invention.
Figure 15B:
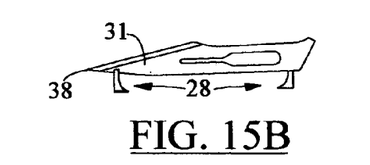
FIG. 15B is a reverse side view of a wire guide system for a scalpel blade, according to an embodiment of the invention.

Also alternatively, the pair of wire guides 28 can be soldered or in some similar way attached, mounted or otherwise adherered to the handle 32 of the scalpel 27. For this alternative, the pair of wire guides are most preferably placed proximate blade end 34 of the handle, with the forward guide 52 proximate to the cutting edge 37 of the blade and the rearward guide 53 further along the handle, toward the butt end 33 of the handle, relative to the forward guide, as shown in FIGS. 12 and 13.

Figure 18:
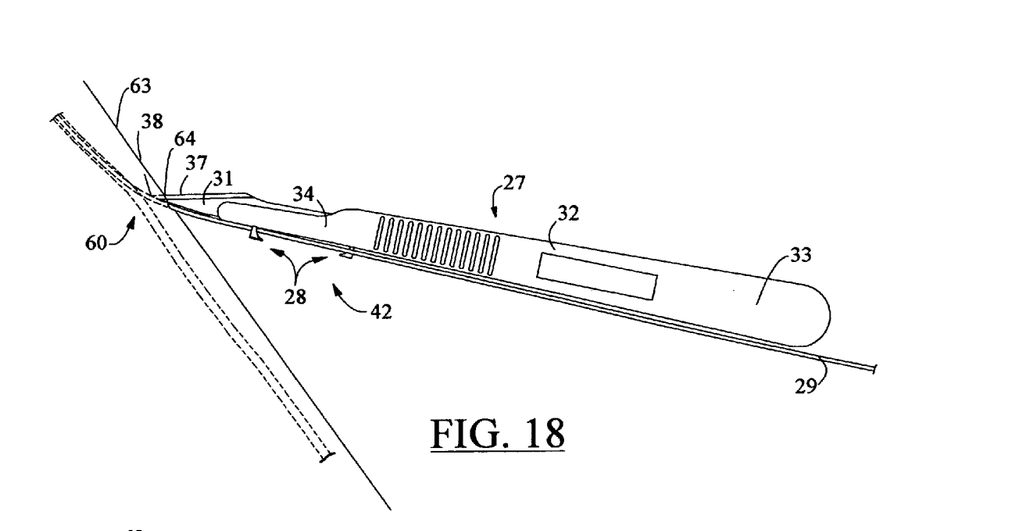
FIG. 18 is a side view of a wire guide system for a scalpel, according to an embodiment of the invention.

For the method of the present invention, the user 26 can easily and with precise control, guides the scalpel 27 on, or along the wire 29, or guidewire, with the scalpel attached to the wire. The user is typically a surgeon, but may be any type of health care professional or such person requiring the use of the scalpel guiding system 25 of the present invention. As a precursor to the attachment of the scalpel to the guidewire, the wire can be introduced into a puncture site 60, as shown in FIG. 18, according to the previously discussed Seldinger technique.

As first discussed above, the scalpel guide system 25 of the present invention is of great benefit in the Seldinger technique, aiding in the percutaneous introduction of a wide variety of catheter devices. In the Seldinger technique, which is well known to those skilled in the surgical arts, a thin-wall percutaneous needle is typically utilized to first puncture a tissue layer 63, at the puncture site. The puncture site is carefully selected to gain entry into a vessel 65, as shown in FIG. 18. The wire 29 is then introduced through the needle, to pass through the tissue layer and gain access into the vessel. Again, the vessel may be any cavity or lumen as appropriate for the Seldinger technique. Additionally, the present invention can be utilized with any diameter of wire conventionally employed in percutaneous procedures that substantially follow the Seldinger technique.

After the wire 29 has been introduced into the puncture site 60 by percutaneous entry, the method of the present invention first includes placing the scalpel 27 proximate to the wire. For the method of the present invention, the wire can either attach to a minimum of the pair of wire guides 28 attached to the scalpel proximate the handle 32, or the blade 31 of the scalpel. If both of the pair of wire guides are attached to the handle, as preferred, a standard scalpel blade can be utilized.

Figure 9A:
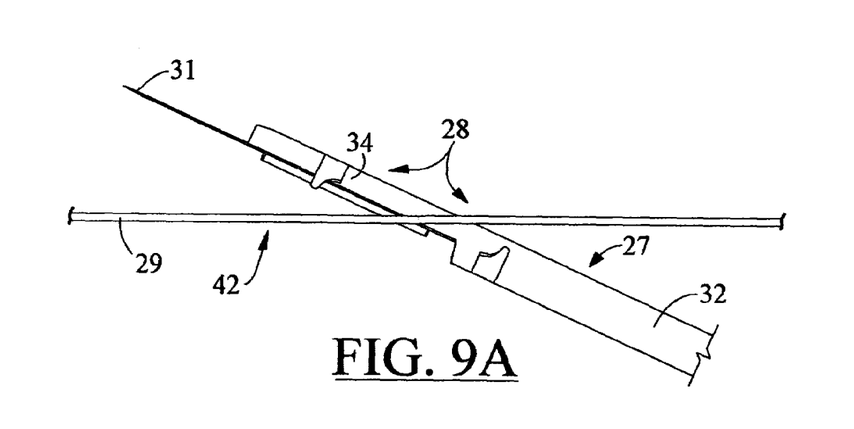
FIG. 9A is a bottom view of a wire guide system for a scalpel, according to an embodiment of the invention.

The placement of the pair of wire guides 28 onto the wire 29 preferably requires the scalpel 27 to be first positioned at an oblique angle to the wire, with the wire running between the pair of wire guides, as shown in FIG. 9A. As discussed previously, the pair of wire guides preferably oppose each other in relation to the wire, so that the wire can contact the inside radius 48 of both the forward guide 52 and the rearward guide 53, when the scalpel is re-oriented parallel to the wire, for attachment of the scalpel to the wire.

Figure 9B:
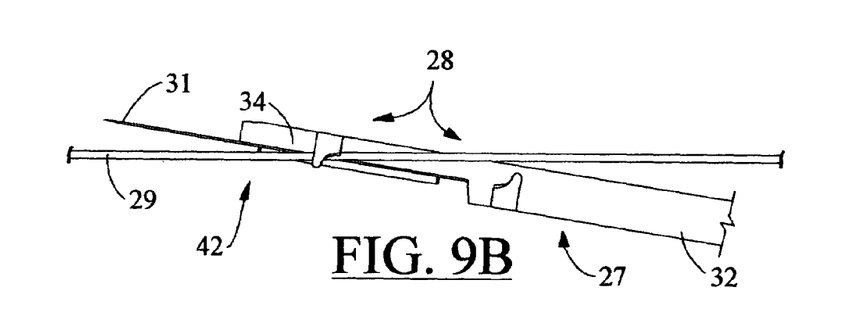
FIG. 9B is a bottom view of a wire guide system for a scalpel, according to an embodiment of the invention.
Figure 9C:
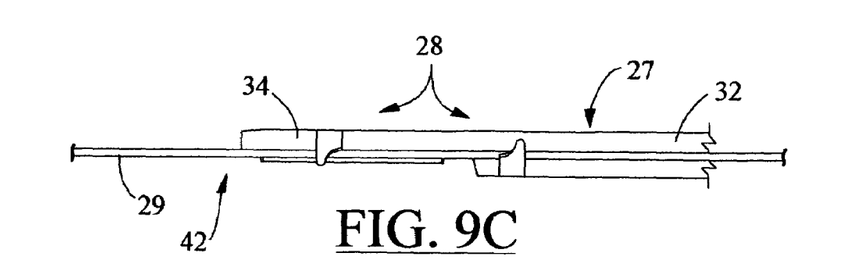
FIG. 9C is a bottom view of a wire guide system for a scalpel, according to an embodiment of the invention.
Figure 10A:
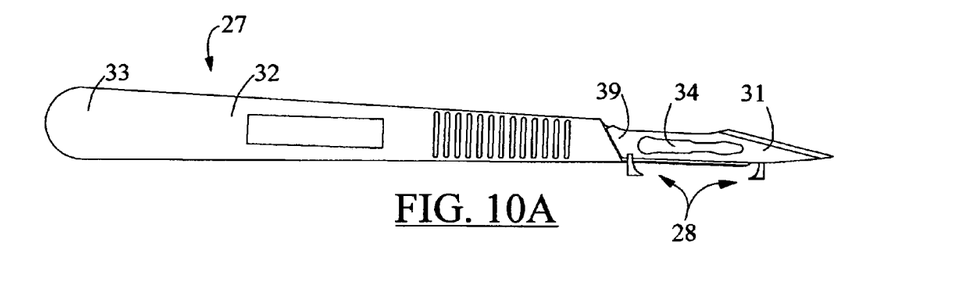
FIG. 10A is a side view of a wire guide system for a scalpel, according to an embodiment of the invention.
Figure 10B:
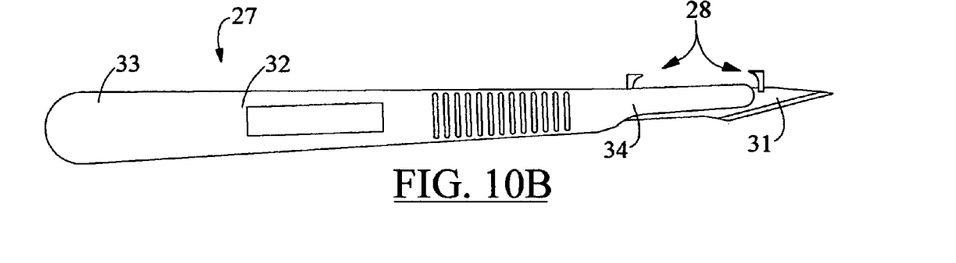
FIG. 10B is a reverse side view of a wire guide system for a scalpel, according to an embodiment of the invention.

The attachment step can additionally include hooking the wire 29 to one of the pair of wire guides 28, say the forward guide 52, as shown in FIG. 9B, and then hooking the wire with the remaining, in this instance, the rearward guide 53, as shown in FIG. 9C. Alternatively, the order of attachment can be reversed, by first hooking the wire with the rearward guide and then hooking the forward guide.

In attachment, the pair of wire guides 28 engage the wire 29, preferably without bending the wire, in that the wire runs through the pair of wire guides without bending or kinking the wire. The pair of wire guides hold the scalpel 27 to the wire, allowing the scalpel to move along the wire, guided by the pair of wire guides. Preferably, the user 26 of the scalpel can then move the scalpel along the wire, the scalpel guided by the wire. Alternatively, the user can either advance or retract both the scalpel and the wire together, as a single unit.

A key step in any percutaneous vascular catheterization requires that the puncture site 60 be enlarged to allow the larger diameter catheter to advance along the wire 29, into the enlarged incision at the puncture site. More broadly, any procedure employing a variation of the Seldinger technique can benefit from the scalpel guiding system 25 of the present invention, with the scalpel re-positionable in a guided movement along a portion of the length of the wire 42.

Figure 19:
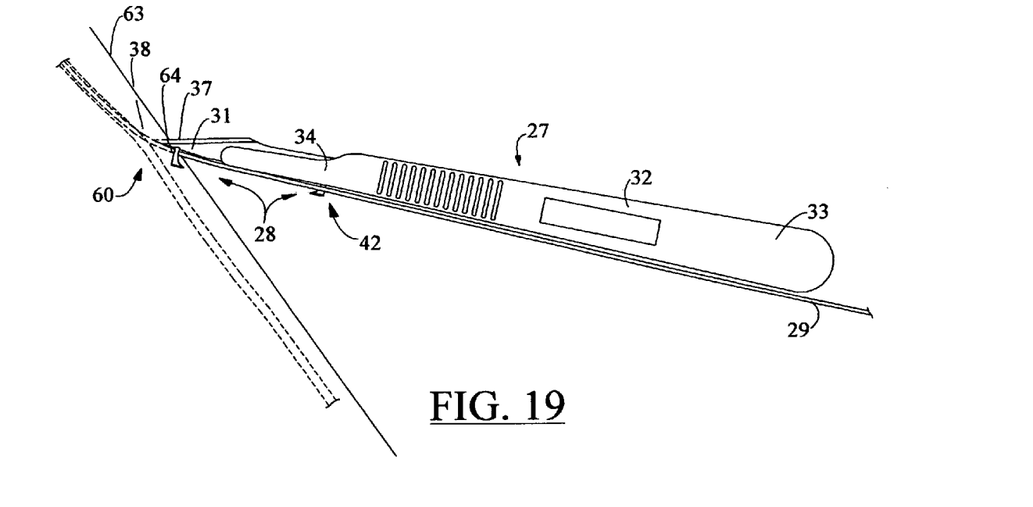
FIG. 19 is a side view of a wire guide system for a scalpel, according to an embodiment of the invention.

By guiding the scalpel 27 down the wire 29 with the aid of the pair of wire guides 28, the blade 31 of the scalpel can incise a tissue layer 63 surface, as shown in FIGS. 18 and 19. The clips orient the scalpel blade against the guidewire in a manner that allows the scalpel blade to be guided by the wire as it is advanced to make a precisely placed dermatology. The standard "#11" blade is preferred for use as the scalpel blade with the present invention because its pointed blade tip easily enlarges the puncture site. Other types of blade, or other blade configurations, could be employed as alternatives to the #11 blade. The pointed tip or point 38 is preferred over rounded tips, but either could be utilized with the system of the present invention.

Since the scalpel 27 is guided by the wire 29, the precise placement of a skin nick 64 by the user 26 is much more easily accomplished, as compared to conventional, unguided methods. The present invention orients the blade 31 of the scalpel against the wire, allowing the user to attach and unattach the scalpel with less concentration than is required to place the skin nick by the unguided free-hand method. The pair of wire guides 28 of the scalpel attach to the wire, without the user placing fingers or hands in front of the blade of the scalpel.

In an additional alternative embodiment of the present invention, a depth stop 68 can be employed as an optional aid to determine a maximum incision depth into the tissue layer 63, at the puncture site 60, as shown in FIG. 19. The scalpel 27 can incorporate the optional depth stop, to prevent the formation of a skin nick 64 that is excessively deep.

In an alternative method of the scalpel guiding system 25, the surgeon, or user 26, the pair of wire guides 28 can be selected or formed to have a low profile, so they will not interfere with the use of the scalpel 27 in the traditional "free-hand" method for forming the skin nick 64 at the puncture site 60, if the user so chooses. Preferably, low profile wire guides will not interfere with the safety shield 40, as shown in FIGS. 3A and 3B and discussed above, available on some of the newer "safety" type of scalpels. Additionally, the pair of wire guides do not interfere with the use of the scalpel to cut the sutures subsequently used to secure any elements proximate to the puncture site.

Figure 20A:
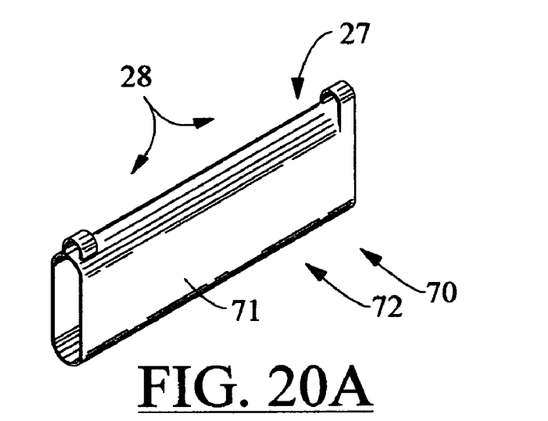
FIG. 20A is a perspective view of a safety shield with a wire guide system for a scalpel, according to an embodiment of the invention.
Figure 20B:
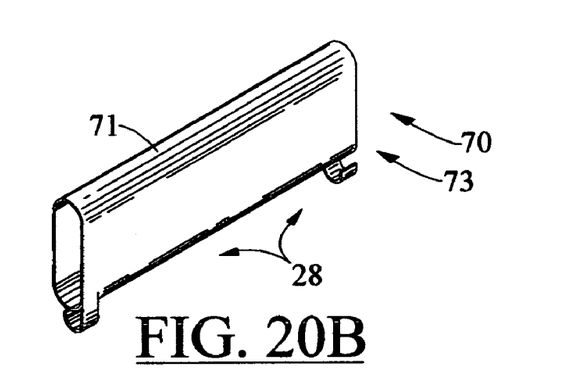
FIG. 20B is a perspective view of a safety shield with a wire guide system for a scalpel, according to an embodiment of the invention.
Figure 20C:
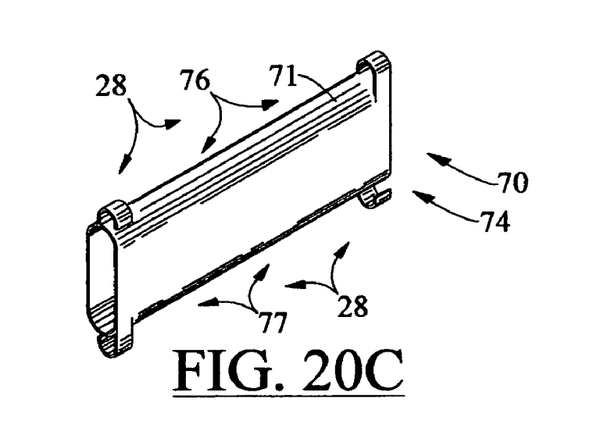
FIG. 20C is a perspective view of a safety shield with a wire guide system for a scalpel, according to an embodiment of the invention.

The conventional safety shield 40, as shown in FIGS. 3A and 3B, is known to be modifiable into a sleeve structure. The present invention can be included in a guided safety sleeve 70, as shown in FIGS. 20A, 20B and 20C. The guided safety sleeve also includes the pair of wire guides 28, which preferably extend from each end of a sleeve body 71 of the guided safety sleeve. As shown in FIG. 20A, the pair of wire guides can extend upward, in an upward guided safety sleeve 72. Alternatively, as shown in FIG. 20B, the pair of wire guides can extend upward, in a downward guided safety sleeve 73. Also alternatively, as shown in FIG. 20C, the pair of wire guides can extend upward, in a combination guided safety sleeve 74. The guided safety sleeve embodiment of the present invention can be used with conventional safety sleeves, as found in protected disposable scalpels, as manufactured for BD Bard-Parker™, by BD Medical Systems of Franklin Lakes, N.J., USA.

In the combination guided safety sleeve 74, as shown in FIG. 20C, two pairs of wire guides 28 are included, an upward oriented pair of wire guides 76, and a downward oriented pair of wire guides 77. The 29 wire can be optionally inserted either in the upward oriented pair of wire guides, or the downward oriented pair of wire guides, depending on the needs of the user 26.

Figure 21A:
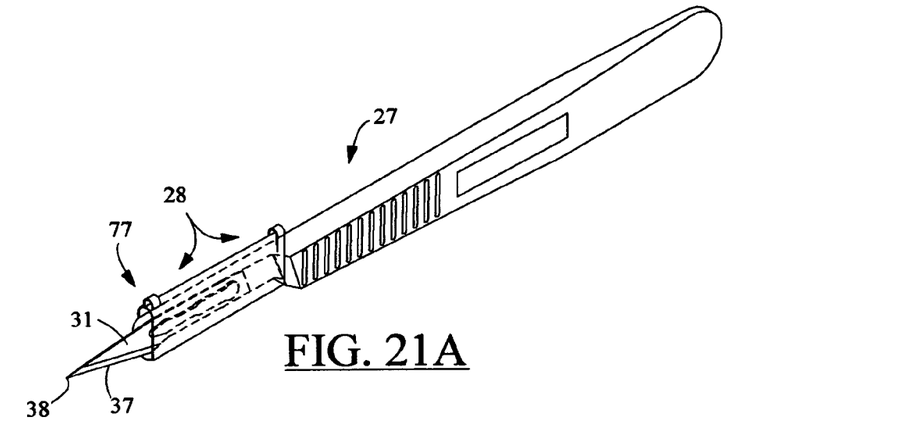
FIG. 21A is a perspective view of a wire guide system for a scalpel, according to an embodiment of the invention.
Figure 21B:
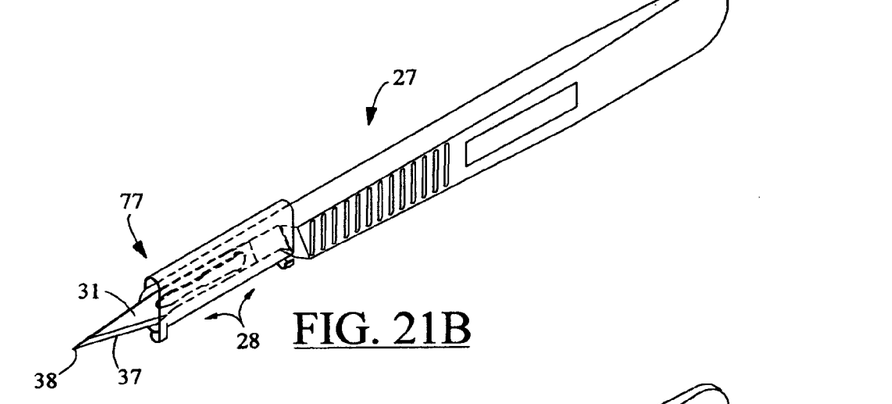
FIG. 21B is a perspective view of a wire guide system for a scalpel, according to an embodiment of the invention.
Figure 21C:
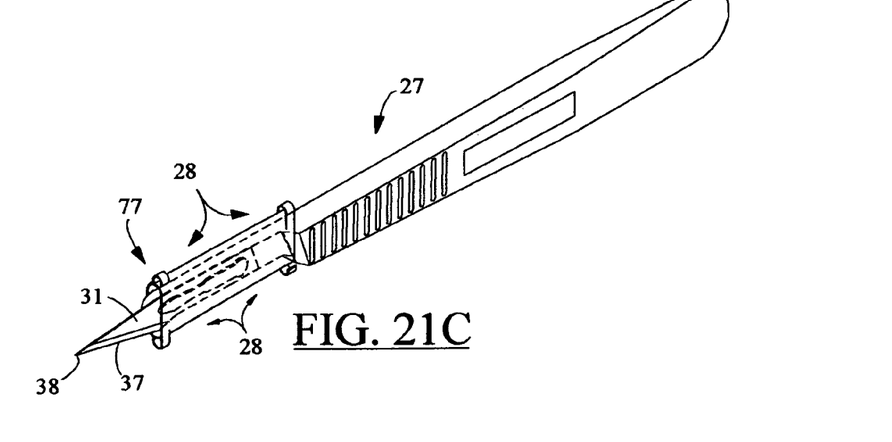
FIG. 21C is a perspective view of a wire guide system for a scalpel, according to an embodiment of the invention.

The sleeve body 71 has a tubular construction and fits over the blade 31 and blade end 34 of the handle 32 of the scalpel 27, to expose the cutting edge 37 and the point 38 of the blade of the scalpel, in an exposed blade position 77, as shown in FIGS. 21A, 21B and 21C. As shown in FIG. 21A, the upward guided safety sleeve 72 can be placed onto the scalpel, with the pair of wire guides 28 extending upward. Alternatively, as shown in FIG. 21B, the downward guided safety sleeve 73 can be placed onto the scalpel, with the pair of wire guides extending downward. Also alternatively, as shown in FIG. 21C, the pair of wire guides can extend both upward and downward, in the combination guided safety sleeve 74.

Figure 22A:
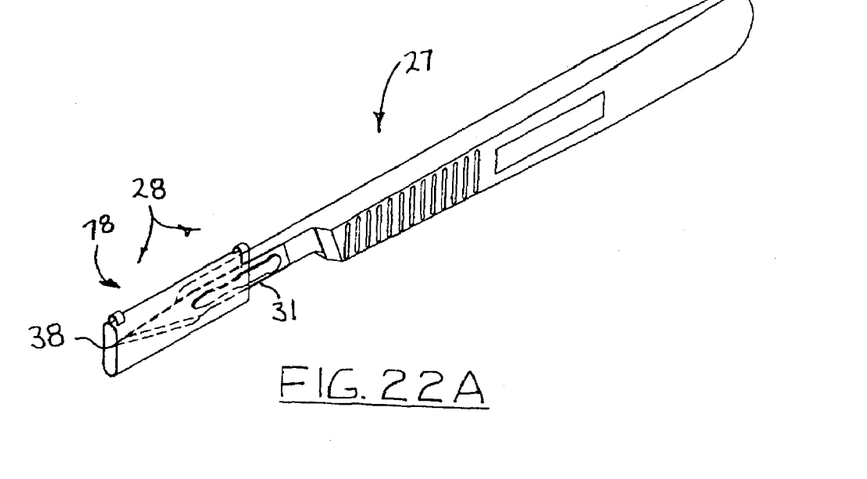
FIG. 22A is a perspective view of a wire guide system for a scalpel, according to an embodiment of the invention.
Figure 22B:
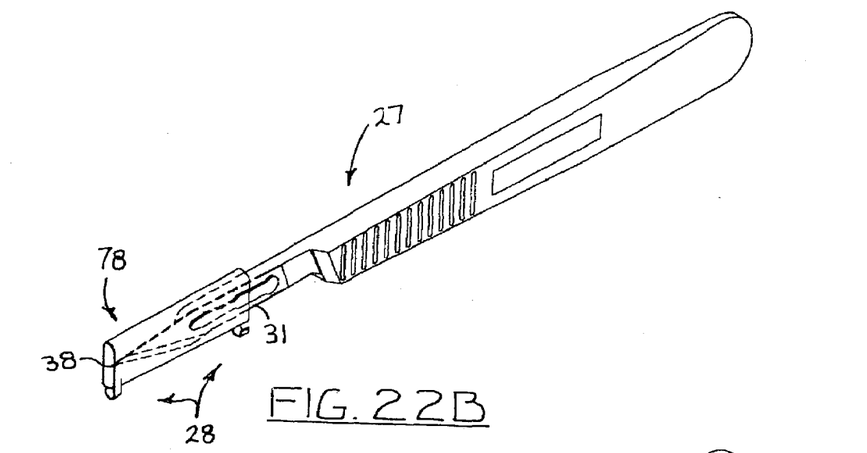
FIG. 22B is a perspective view of a wire guide system for a scalpel, according to an embodiment of the invention.
Figure 22C:
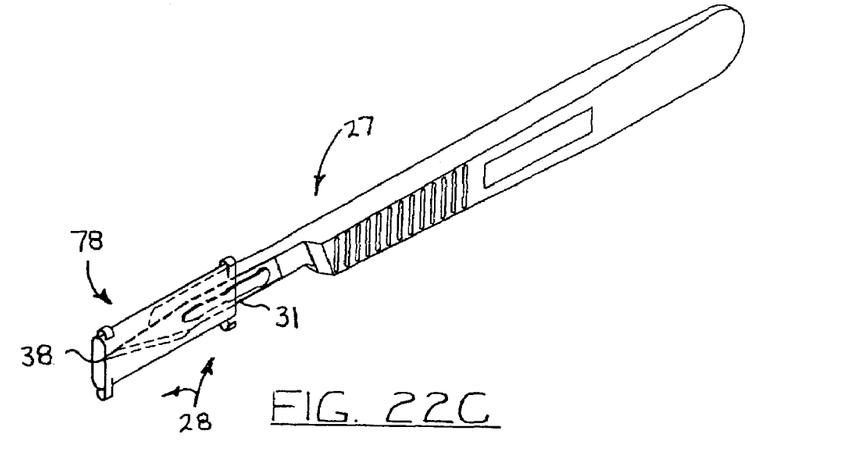
FIG. 22C is a perspective view of a wire guide system for a scalpel, according to an embodiment of the invention.

Each embodiment of the guided safety sleeve 70 covers the cutting edge 37 and the point 38 of the blade 33 of the scalpel 27, as a safe covering of these sharp portions of the scalpel. This coverage minimizes the possibility of injuries from the blade, by inadvertent nicks or pokes. As shown in FIGS. 22A, 22B and 22C, the guided safety sleeve can slidably extend to cover these sharp portions of the scalpel, in a safety position 78. As an alternative, the sleeve body need not be a continuous sleeve, as shown, but a three sided sleeve that leaves the non-sharpened edge of the blade exposed.

A locking mechanism can also be employed with the guided safety sleeve 70, as used in conventional, sliding scalpel shields. The locking mechanism, serves to lock the sleeve body 71 in place, to expose the cutting edge and point in the exposed blade position 77, or the safety position 78, discussed above. As an additional alternative, the guided safety sleeve can be slid to an intermediate position, between the exposed blade position and the safety position. Especially if locked in place, the intermediate positioned sleeve can be utilized as a sleeve depth stop, serving a similar purpose to the depth stop 68, employed as an optional aid to determine a maximum incision depth into the tissue layer 63.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible, which employ the same inventive concepts as described above. Therefore, the invention is not to be limited except by the following claims, as appropriately interpreted in accordance with the doctrine of equivalents.

The following is claimed:

1. A scalpel guide system comprising:
   a pair of wire guides, each extending from a scalpel;
   the scalpel includes a handle; and the pair of wire guides include a pair of hooks, and the pair of hooks extend from the scalpel handle;
   a wire having a length, the wire engaged by the pair of wire guides along a continuous length of the wire, without threading an end of the wire through the pair of wire guides, the wire held by the pair of wire guides in an attachment parallel to the scalpel with the wire held external from the scalpel; and
   the scalpel re-positionable in a guided movement along a portion of the length of the wire.

2. The scalpel guide of claim 1, wherein;
   the scalpel is removably attachable from to the length of the wire, without threading the end of the wire through the pair of wire guides.

3. A scalpel guide system comprising:
   a pair of wire guides, each extending from a scalpel;
   a wire having a length, the wire engaged by the pair of wire guides; the pair of wire guides, each having a hooked shape and each attachable to the length of the wire without threading an end of the wire through the pair of wire guides; and
   the scalpel re-positionable in a guided movement along a portion of the length of the wire.

4. The scalpel guide of claim 3, wherein;
   the scalpel includes a scalpel handle; and
   the pair of wire guides each extend from the scalpel handle.

5. The scalpel guide of claim 3, wherein;
   the pair of wire guides include a forward guide and a rearward guide;
   the scalpel includes a scalpel handle; and
   the rearward guide of the pair of wire guides extends from the scalpel handle.

6. The scalpel guide of claim 3, wherein;
   the pair of wire guides include a forward guide and a rearward guide; and
   the forward guide functions as a depth stop for the scalpel.

7. An improved scalpel system of the type having a singular blade attached to a handle, the blade including a cutting edge, a point and a shank, the shank of the blade received into the handle, the handle of the scalpel including a butt end and a blade end, the butt end at a termination of the handle, and the handle graspable by a user of the scalpel, the improvement comprising:
   a pair of wire guides engaging wire along a length of the wire in a parallel attachment to the wire, and each of the pair of wire guides emends from the scalpel;
   the pair of wire guides include a pair of hooks;
   the pair of wire guides include a forward guide and a rearward guide, the forward guide opposed to the rearward guide in relation to the wire in the parallel attachment; and
   the wire engageable with the pair of wire guides, without threading an end of the wire through the forward guide and without threading an end of the wire through the rearward guide.

8. The improved scalpel of claim 7, wherein;
   the wire is held externally to the handle and the is wire held externally to the blade; and
   the wire is engaged by the pair of wire guides.

9. The improved scalpel of claim 7, wherein;
   the scalpel is removably attachable to the wire, without threading an end of the wire through the forward guide and without threading an end of the wire through the rearward guide.

10. The improved scalpel of claim 9, wherein;
    the wire has a length, the wire engageable by the pair of wire guides by hooking a portion of the length of the wire in a substantially parallel relation to the pair of wire guides; and
    the scalpel re-positionable in a guided movement along a portion of the length of the wire.

11. The scalpel guide of claim 7, wherein;
    the forward guide functions as a depth slop for the blade of the scalpel.

* * * * *